United States Patent [19]

Devaine et al.

[11] Patent Number: 5,759,531
[45] Date of Patent: Jun. 2, 1998

[54] SHAVING GEL WITH DELAYED FOAMING COMPRISING A MONOESTER OF C4-C10 ACID AND OF C16-C18 ALCOHOL

[75] Inventors: André Devaine, Goussainville; Alain Caudet, Meudon, both of France

[73] Assignee: L'Oreal, Paris, France

[21] Appl. No.: 657,442

[22] Filed: Jun. 3, 1996

[30] Foreign Application Priority Data

Jun. 2, 1995 [FR] France .................. 95 06608

[51] Int. Cl.⁶ .................................................. A61K 7/15
[52] U.S. Cl. ................ 424/73; 424/43; 514/944
[58] Field of Search .............................. 424/73, 43

[56] References Cited

FOREIGN PATENT DOCUMENTS

| 0259843 | 9/1987 | European Pat. Off. . |
| 0339634 | 4/1989 | European Pat. Off. . |
| 1961146 | 12/1969 | Germany . |
| 95/05147 | 8/1994 | WIPO . |

*Primary Examiner*—Thurman K. Page
*Assistant Examiner*—James M. Spear
*Attorney, Agent, or Firm*—Finnegan, Henderson, Farabow, Garrett & Dunner, L.L.P.

[57] ABSTRACT

An aqueous shaving gel with delayed foaming comprising a water-soluble soap, a so-called "delayed-effect" volatile foaming agent and optionally a water-soluble gelling polymer, and including at least one specific ester which is a monoester of $C_4$–$C_{10}$ aliphatic acid and of $C_{16}$–$C_{18}$ aliphatic alcohol.

22 Claims, No Drawings

SHAVING GEL WITH DELAYED FOAMING COMPRISING A MONOESTER OF C4-C10 ACID AND OF C16-C18 ALCOHOL

The present invention relates to a new aqueous shaving gel with delayed foaming comprising a water-soluble soap, a so-called "delayed-effect" volatile foaming agent and optionally a water-soluble gelling polymer, and essentially including a specific ester which is a monoester of $C_4$–$C_{10}$ aliphatic acid and of $C_{16}$–$C_{18}$ aliphatic alcohol.

Gels with delayed foaming (or with a delayed foam effect) are already known in the cosmetic field, especially in their applications as shaving gels, and have been described in many patents such as, for example, U.S. Pat. No. 3,541,581, U.S. Pat. No. 4,405,489, and FR 2 595 943 (the disclosures of which are specifically incorporated by reference herein).

These gels with a delayed foam effect are compositions which are generally packaged under pressure in an aerosol device which, under the effect of a propellant, delivers gels which are nonfoaming in static conditions but which, under the mechanical action due to the spreading of the product on the skin, spontaneously and virtually instantaneously produce a foam on the latter.

Aqueous shaving gels with delayed foaming should exhibit numerous characteristics which make their development particularly difficult.

First of all, the gel delivered into the hand should exhibit an appropriate rheology (rigidity, consistency). In addition, when spread onto the skin of the face, this gel should be capable of very rapidly developing a foam, itself capable of acquiring volume without, however, producing small accumulations of rigid foam. Finally, the foam generated by the gel should be endowed with good cosmetic qualities, such as contribution of softness and the absence of a sticky effect and/or of a fluid effect on the skin.

Unfortunately, the delayed-foaming shaving gel compositions of the prior art generally do not meet all these conditions.

To facilitate the use and to increase the stability of such gels it has already been proposed to introduce therein alkanolamides of $C_{12}$–$C_{18}$ fatty acids or ethoxylated fatty alcohols, or else propylene glycol dipelargonate. There again, however, in view of the properties listed above, the gels obtained have not yet been found completely satisfactory.

The present invention aims to propose shaving gels with delayed foaming exhibiting improved properties.

Thus, after numerous investigations carried out into the question, the inventors have now discovered, completely unexpectedly and surprisingly, that by adding a monoester of $C_4$–$C_{10}$ aliphatic acid and of $C_{16}$–$C_{18}$ aliphatic alcohol to the composition of a conventional shaving gel comprising, in aqueous medium, (a) a water-soluble soap, (b) a so-called "delayed-effect" volatile foaming agent and (c) optionally a water-soluble gelling polymer, it is possible to obtain a gel exhibiting improved performance and/or properties, particularly with respect to the characteristics described above.

This discovery underlies the present invention.

The subject-matter of the present invention is thus a new aqueous shaving gel with delayed foaming comprising a water-soluble soap, a so-called "delayed- effect" volatile foaming agent and optionally a water-soluble gelling polymer, and including at least one monoester of $C_4$–$C_{10}$ aliphatic acid and of $C_{16}$–$C_{18}$ aliphatic alcohol.

The monoester(s) of $C_4$–$C_{10}$ aliphatic acids and of $C_{16}$–$C_{18}$ aliphatic alcohols which may be employed according to the invention are preferably chosen from the monoesters of $C_4$–$C_{10}$ linear or branched saturated aliphatic acids and of $C_{16}$–$C_{18}$ linear saturated aliphatic alcohols.

Monoesters of this type which are more particularly preferred according to the present invention are the ester of heptanoic acid and stearyl alcohol (or stearyl heptanoate), the ester of octanoic acid and of stearyl alcohol (or stearyl octanoate) or else stearyl heptanoate/octanoate mixtures, in particular the stearyl heptanoate (67%)/octanoate (33%) mixture sold, for example, by the Croda company under the trade name Crodamol W or by the company Stearineries Dubois under the trade name Dub Solide.

The other constituents forming part of the composition of the shaving gels with delayed foam effect in accordance with the invention are products which are already known per se in the application in question (see, in this context, EP-A-259 843, U.S. Pat. No. 3,541,581 and FR 2 595 943, the disclosures of which are specifically incorporated by reference herein).

The water-soluble soap is preferably a water-soluble fatty acid salt. Such soaps are known in the prior art, exist in the trade or can be prepared according to conventional methods, for example by the reaction of a base, such as triethanolamine, directly with a fatty acid, such as a $C_{10}$–$C_{22}$ saturated or unsaturated fatty acid, or mixtures of these acids. Preferred soaps according to the invention include water-soluble stearates, myristates and palmitates, such as the soluble amine soaps of commercial stearic or palmitic acids. The triethanolamine salts of these acids are more particularly preferred. It is well known, furthermore, that the commercial product sold under the name of stearic acid may be a mixture of stearic and palmitic acids. The term "stearates" denotes the soaps of commercial stearic acid, but may also denote the soaps of pure stearic acid.

A water-soluble soap which is particularly preferred according to the invention is triethanolamine palmitate.

When a water-soluble gelling polymer is employed according to the invention, it may be chosen from water-soluble hydroxyalkyl celluloses or natural gums such as xanthan gum. Hydroxyalkyl celluloses are manufactured from an alkyl cellulose and an alkylene oxide such as ethylene oxide or propylene oxide.

Products of this type are sold under the trademarks "Klucel" and "Natrosol" in a range of various viscosities.

A water-soluble polymer which is more particularly preferred according to the present invention is a hydroxypropyl cellulose sold under the trademark "Klucel H" or "Klucel MF" by the company Aqualon, a hydroxyethyl cellulose sold under the trademark "Natrosol 250 HHR" by the company Aqualon, or a mixture of these two celluloses.

One of the advantages associated with the present invention is that it is possible to reduce, or even eliminate, the quantity of cellulose-based thickener, the excessive proportions of which are at the source of the disadvantage of stickiness on the skin.

The delayed-foaming agent is liquid or liquefiable and volatile at the temperature of the skin. It includes saturated aliphatic hydrocarbons containing from 4 to 6 carbon atoms, such as butanes, n-butane or isobutane, pentanes such as n-pentane or isopentane, or else hexane. Mixtures of these hydrocarbons may be employed to obtain the desired vapour pressure.

A delayed-foaming agent which is particularly well suited for controlling the pressure of the gel with a view to obtaining the foam properties required for the present invention is the mixture isopentane (75% by weight)/isobutane (25% by weight).

Water, present in the gel composition according to the invention, takes part in the required foam properties and is used to moisten the skin and to ensure suitable shaving.

In the shaving gels with delayed foaming according to the present invention the monoester of $C_4$-$C_{10}$ aliphatic acid and of $C_{16}$-$C_{18}$ aliphatic alcohol is generally present in weight concentrations (referred to the whole of the composition) ranging from 0.5 to 5%, preferably ranging from 1.5 to 3%, the water-soluble soap is generally present in weight concentrations ranging from 5 to 20%, preferably ranging from 10 to 15%, the water-soluble gelling polymer may be generally present in weight concentrations ranging from 0 to 3%, preferably ranging from 0 to 1% depending on the viscosity of the product employed, the delayed-foaming agent is generally present in weight concentrations ranging from 0.5 to 10%, preferably ranging from 2 to 5%, and water is generally present in weight concentrations ranging from 60 to 90%, relative to the total weight of the compositions.

The shaving gel with delayed foaming according to the invention may further contain other ingredients or active substances which are well known in the field of shaving products, such as, for example, hydrating agents, to mention only a few thereof, glycerine and sorbitol, thickening agents such as allantoin or α-bisabolol, lubricants such as silicones or polydecenes, emollients like polyethylene glycol, polypropylene glycol or glycerol monostearate, surface-active agents, vitamins, solvents, colorants, perfumes and preserving agents.

A person skilled in the art chooses this or these optional complementary compound(s) such that the advantageous properties intrinsically associated with the gel in accordance with the invention are not, or are substantially not, adversely affected by the addition or additions envisaged.

The gels according to the invention may be packaged in the form of tubes or aerosols, according to techniques which are well-known to a person skilled in the art and are described in particular in U.S. Pat. No. 3,541,581 (the disclosure of which is specifically incorporated by reference herein).

The aerosol devices may have a single or double container.

In the double-container aerosol devices, the propellant system is separated from the gel in accordance with the invention. In fact, the gel in accordance with the invention is introduced into the middle part of the double-container aerosol, and the propellant is introduced into the outer container, which is separated from the middle part by a diaphragm which is a compressible plastic membrane.

In such double-container devices, the propellant system may then comprise a condensable gas such as a hydrocarbon like propane, butane, isobutane, isopentane, halogenated hydrocarbons or dimethyl ether or else mixtures of these compounds. It may also include a mixture of these condensable propellent agents with noncondensable gases such as nitrous oxide or nitrogen.

In single-container devices, the propellant system comprises only noncondensable gases which are insoluble in the gel in accordance with the invention, such as nitrogen, argon, neon, krypton, xenon, helium, radon, nitrous oxide or carbon dioxide.

Such devices are equipped with a dip tube into the upper part of which the said propellant system is introduced. In this case, the propellant system which is noncondensable and insoluble in the gel in accordance with the invention acts as a plunger and expels the gel via the dip tube.

In the aerosols, the gel in the pressurized state (or "juice") advantageously represents from 90 to 98% of the weight of the whole composition, and the propellant system from 2 to 10% of this weight.

The gels according to the invention can be employed for shaving hair present on human or animal skin.

Concrete, but nonlimiting examples illustrating the invention will now be given.

EXAMPLE 1

A shaving gel with delayed foaming was prepared as follows:

(i) 97 grams of the following composition were introduced into the middle part of a double-container aerosol device:

| | |
|---|---|
| Palmitic acid | 7.5 g |
| Stearic acid | 2.5 g |
| Sorbitol | 2.0 g |
| Propylene glycol | 2 g |
| Hydroxyethyl cellulose (Natrosol 250 HHR from the company Aqualon) | 0.25 g |
| Surfactant: triethanolamine lauryl ether sulphate | 2.5 g |
| Polydimethylsiloxane | 1 g |
| Stearyl heptanoate (67%)/octanoate (33 %) (Dub Solide from the company Stearineries Dubois). | 3 g |
| Triethanolamine | 7.5 g |
| Demineralized water q.s. | 100 g | followed by (ii) 3 grams of the delayed-foaming agent comprising an isopentane (75% by weight)/isobutane (25% by weight) mixture.

The middle part was closed. Pressurization of the mixture obtained above or "juice" was then carried out by introducing into the lower part of the double container and via the bottom opening, 4 to 10 grams of a propellant comprising an isobutane (55% by weight), butane (22%), propane (23%) mixture sold under the name Aerogaz 3.2N by the company Elf Aquitaine.

The crimped aerosol was then ready to be employed. When it was brought into action, it delivered into the hand a gel with a rheology such that it was given a rigidity enabling it to stay firm in the hand and to spread easily in a homogeneous manner on the skin of the face without giving rise to small accumulations of foam. Under the mechanical action of the spreading on the skin, the gel rapidly developed a foam, which was soft in application, smooth and uniform, which did not stick to the skin and did not run. After shaving the skin was soft and smooth.

EXAMPLE 2

A shaving gel with delayed foaming was prepared as follows:

(i) 97 grams of the following composition were introduced into the middle part of a double-container aerosol device:

| | |
|---|---|
| Palmitic acid | 12 g |
| Myristic acid | 3 g |
| Glycerine | 1 g |
| Glycerol monostearate | 0.1 g |
| Surfactant: octylphenol oxyethylenated with 5 moles of ethylene oxide | 2 g |
| Polydecene (Silkflo S 362 NF from the company Albemarle) | 1 g |
| Stearyl heptanoate (67 %)/octanoate (33 %) (Dub Solide from the company Stearineries Dubois). | 3 g |
| Triethanolamine | 9 g |
| Demineralized water q.s. | 100 g | followed by (ii) 3 grams of a delayed-foaming agent comprising an isopentane (75% by weight)/isobutane (25% by weight) mixture.

The middle part was closed. Pressurization of the juice was then performed in the same manner as following Example 1.

The shaving gel thus prepared was applied in the same way as in the preceding example and exhibited the same properties.

EXAMPLE 3

A shaving gel with delayed foaming was prepared in the following manner:

(i) 97 grams of the following composition were introduced into the middle part of a double-container aerosol device:

| | |
|---|---|
| Palmitic acid | 11 g |
| Triethanolamine | 8.5 g |
| Glycerine | 4 g |
| Hydroxypropyl cellulose (Klucel MF from the company Aqualon) | 0.2 g |
| Polyethylene glycol (Polyox WSR 205 from the company Amerchol) | 0.3 g |
| Stearyl heptanoate (67%)/octanoate (33%) (Dub Solide from the company Stearineries Dubois). | 3 g |
| Polydimethylsiloxane | 1 g |
| α-Bisabolol | 0.1 g |
| Demineralized water q.s | 100 g | followed by (ii) 3 grams of a delayed-foaming agent comprising an isopentane (75% by weight)/isobutane (25% by weight) mixture. The middle part was closed.

Pressurization of the juice was then carried out in the same way as following Example 1, but by employing 4 to 6 grams of a propellant comprising isobutane sold under the name Aeron Isobutane by the company Klockner.

The shaving gel thus prepared was employed in the same way as in the preceding examples and had the same properties.

We claim:

1. An aqueous shaving gel with delayed foaming, comprising: at least one water-soluble soap,
    at least one volatile delayed-foaming agent,
    at least one monoester of $C_4$–$C_{10}$ aliphatic acid and of $C_{16}$–$C_{18}$ aliphatic alcohol, and
    optionally, a water-soluble gelling polymer or a mixture of water-soluble gelling polymers.

2. A gel according to claim 1, wherein said at least one monoester of $C_4$–$C_{10}$ aliphatic acid and of $C_{16}$–$C_{18}$ aliphatic alcohol is selected from the monoesters of $C_4$–$C_{10}$ linear or branched saturated aliphatic acids and of $C_{16}$–$C_{18}$ linear saturated aliphatic alcohols.

3. A gel according to claim 2, wherein said at least one monoester is selected from stearyl heptanoates or stearyl octanoates.

4. A gel according to claim 3, wherein said at least one monoester is a stearyl heptanoate/octanoate mixture.

5. A gel according to claim 1, wherein said at least one water-soluble soap is a water-soluble fatty acid salt.

6. A gel according to claim 5, wherein said at least one water-soluble fatty acid salt is selected from the salts of stearic acid, myristic acid, or palmitic acid.

7. A gel according to claim 6, wherein said at least one soap is selected from the triethanolamine salts of stearic acids, myristic acids, or palmitic acids.

8. A gel according to claim 1, wherein said at least one volatile delayed-foaming agent is selected from butanes, pentanes, or hexanes.

9. A gel according to claim 8, wherein said at least one volatile delayed-foaming agent is a mixture of isopentane and isobutane.

10. A gel according to claim 1, wherein said at least one gelling polymer is selected from water-soluble hydroxyalkyl celluloses.

11. A gel according to claim 10, wherein said water-soluble hydroxyalkyl celluloses are selected from hydroxypropyl celluloses or hydroxyethyl celluloses.

12. A gel according to claim 1, wherein said at least one monoester is present in a weight concentration ranging from 0.5 to 5% by weight relative to the total weight of the composition.

13. A gel according to claim 12 wherein said at least one monoester is present in a weight concentration ranging from 1.5 to 3% by weight relative to the total weight of the composition.

14. A gel according to claim 1, wherein said at least one soap is present in a concentration ranging from 5 to 20% by weight relative to the total weight of the composition.

15. A gel according to claim 14, wherein said at least one soap is present in a concentration ranging from 10 to 15% by weight relative to the total weight of the composition.

16. A gel according to claim 1, wherein said at least one volatile delayed-foaming agent is present in a concentration ranging from 0.5 to 10% by weight relative to the total weight of the composition.

17. A gel according to claim 16, wherein said at least one volatile delayed-foaming agent is present in a concentration ranging from 2 to 5% by weight relative to the total weight of the composition.

18. A gel according to claim 1, wherein said gel comprises at least one gelling polymer present in a concentration ranging from 0 to 3% by weight relative to the total weight of the composition.

19. A gel according to claim 18, wherein said at least one gelling polymer is present in a concentration ranging from 0 to 1% by weight relative to the total weight of the composition.

20. A gel according to claim 1, wherein water is present in a proportion ranging from 60 to 90% by weight relative to the total weight of the composition.

21. A gel according to claim 1, wherein said gel is in a pressurized state in the form of an aerosol.

22. A method of shaving hair comprising the steps of applying to hair-bearing skin a gel according to claim 1 and thereafter shaving said hair.

* * * * *